(12) United States Patent
Yoshida et al.

(10) Patent No.: US 11,337,666 B2
(45) Date of Patent: May 24, 2022

(54) X-RAY FLUOROSCOPIC IMAGING APPARATUS

(71) Applicant: SHIMADZU CORPORATION, Kyoto (JP)

(72) Inventors: Koki Yoshida, Kyoto (JP); Daisuke Murakami, Kyoto (JP); Dai Hirose, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/878,623

(22) Filed: Jan. 24, 2018

(65) Prior Publication Data
US 2018/0256125 A1 Sep. 13, 2018

(30) Foreign Application Priority Data
Mar. 10, 2017 (JP) .............................. JP2017-045818

(51) Int. Cl.
A61B 6/04 (2006.01)
A61B 6/00 (2006.01)
G01N 23/04 (2018.01)

(52) U.S. Cl.
CPC ............ *A61B 6/487* (2013.01); *A61B 6/0407* (2013.01); *A61B 6/4441* (2013.01); *A61B 6/467* (2013.01); *G01N 23/043* (2013.01); *A61B 6/54* (2013.01)

(58) Field of Classification Search
CPC ......... A61B 6/0407; A61B 6/035; A61B 6/04; G01N 23/046; H01J 2237/20278; H01J 2237/20235; H01J 2237/20228; H01J 2237/20221; H01J 2237/202; H01J 2237/2007; H01J 2237/20
See application file for complete search history.

(56) References Cited

U.S. PATENT DOCUMENTS 6,522,713 B1 * 2/2003 Valiga .................... A61B 6/032
378/4
6,552,713 B1 * 4/2003 Van Brocklin ....... G06F 1/1616
345/156
2005/0234327 A1 * 10/2005 Saracen ................ A61B 6/548
600/407

(Continued)

FOREIGN PATENT DOCUMENTS

CN 10249196 A 8/2012
JP 11-285491 10/1999

(Continued)

OTHER PUBLICATIONS

JP 2017-045818, Reasons for Refusal, dated May 18, 2020, 5 pages—Japanese, 5 pages—English.

(Continued)

*Primary Examiner* — David P Porta
*Assistant Examiner* — Mamadou Faye
(74) *Attorney, Agent, or Firm* — Andrew F. Young; Nolte Lackenbach Siegel

(57) ABSTRACT

An X-ray fluoroscopic imaging apparatus includes an operation element that includes a motion axis selection switch and a plurality of direction switches; and a control element that controls a shifting of a relative location between an imaging element and a table relative to a motion-axis by the motion-axis selection switch to a shiftable predetermined motion-axis mode.

9 Claims, 13 Drawing Sheets

(56) References Cited

U.S. PATENT DOCUMENTS

| | | | | |
|---|---|---|---|---|
| 2012/0109608 A1* | 5/2012 | Core | ...................... | G16H 50/50 |
| | | | | 703/6 |
| 2015/0201891 A1* | 7/2015 | Padwa | ................... | A61B 6/032 |
| | | | | 600/425 |
| 2018/0070911 A1* | 3/2018 | Franklin | .............. | A61B 6/4429 |
| 2018/0243149 A1 | 8/2018 | Yano et al. | | |

FOREIGN PATENT DOCUMENTS

| | | |
|---|---|---|
| JP | 2006-149858 | 6/2006 |
| JP | 2010-46315 | 3/2010 |
| JP | 2013-215247 | 10/2013 |
| JP | 2015-223245 | 12/2015 |
| JP | 2017-045818 | 3/2017 |
| JP | 2018-139798 | 9/2018 |

OTHER PUBLICATIONS

Chinese Patent No. 201810096488.0, Office Action dated Feb. 26, 2021, 8 pages—Chinese; 6 pages—English.

* cited by examiner

*FIG. 10A* *FIG. 10B*
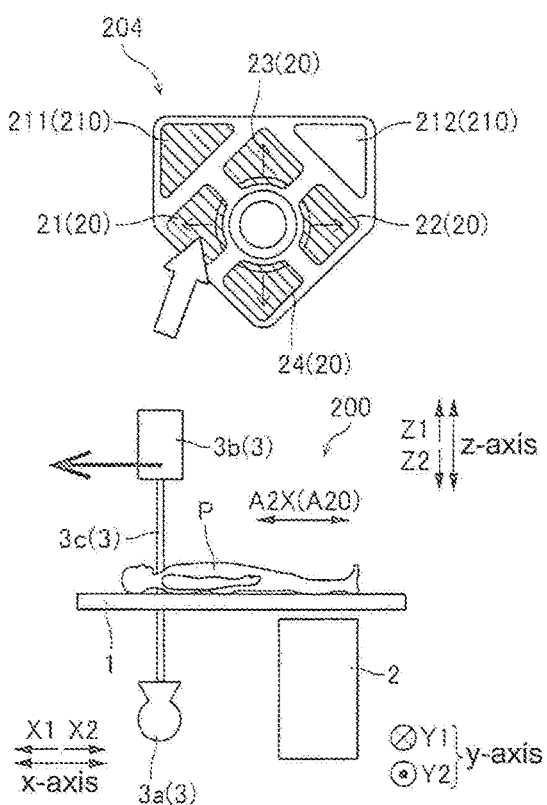
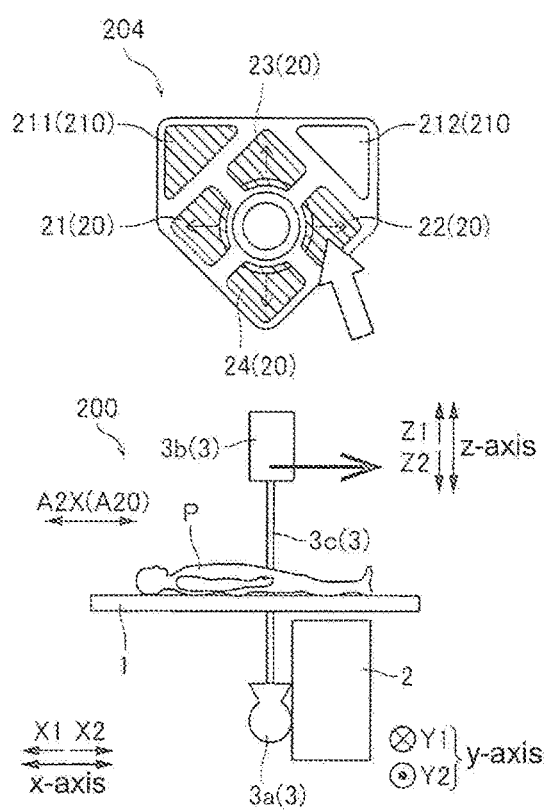

X-RAY FLUOROSCOPIC IMAGING APPARATUS

CROSS REFERENCE TO RELATED APPLICATIONS

This application relates to, and claims priority from JP 2017-045818 filed Mar. 10, 2017, the entire contents of which are incorporated herein by reference.

FIGURE SELECTED FOR PUBLICATION

FIG. 1A, 1B

BACKGROUND OF THE INVENTION

Field of the Invention

The present invention relates to an X-ray fluoroscopic imaging apparatus.

Description of the Related Art

Conventionally, an X-ray fluoroscopic imaging apparatus capable of moving a table relative to a plurality of motion axes is known. Such X-ray fluoroscopic imaging apparatus is disclosed in Patent Document JP2015-223245 A1.

The Patent Document JP2015-223245 A1 discloses the X-ray fluoroscopic imaging apparatus that comprises: the table that loads the subject (test specimen); the imaging system (imaging element) having the X-ray tube and X-ray detector; the rotation mechanism (shifting mechanism) that rotates the table and the imaging system together; the lifting mechanisms that lifts the table and the imaging system together along the axis (motion-axis) extending in the perpendicular direction; and the imaging system shifting mechanism (shifting mechanism) that shifts the imaging system in the longitudinal direction relative to the table. According to the X-ray fluoroscopic imaging apparatus disclosed in the Patent Document JP2015-223245 A1, the rotation mechanism rotates the table around the center that is an axis (motion-axis) extending in the orthogonal direction to the longitudinal direction of the table and also the horizontal direction. In addition, according to the X-ray fluoroscopic imaging apparatus disclosed in the Patent Document JP20115-223245 A1, the input element (operation element) comprises: the rotation operation lever (direction switch) that rotates the table and the imaging system; the up-button (direction switch) and the down-button (direction switch) that shift the table and the imaging system up-and-down; and the imaging system operation lever (direction switch) that shifts the imaging system in the longitudinal direction of the table.

According to the X-ray fluoroscopic imaging apparatus disclosed in the Patent Document JP2015-223245 A1 and so forth, each direction switch is installed relative to each plurality of motion-axes, so that the more motion-axes are, the more switches are. Therefore, it is problematic that; the number of switch increases and as a result, the operation element is larger and disturbs an examination and a treatment, and the desired switch is hardly comprehended, so that the prompt operation can be dragged.

In addition, according to the X-ray fluoroscopic imaging apparatus disclosed in the Patent Document JP2015-223245 A, when the operator erroneously operates the direction switch during the examination and the treatment, it is problematic that the imaging system or the table is shifted unintentionally.

ASPECTS AND SUMMARY OF THE INVENTION

The present invention intends to solve the problem as set forth above and one of the purposes of the present invention is to provide an X-ray fluoroscopic imaging apparatus capable of limiting growing of the operation element in size, improving an operability thereof, and in addition, preventing the unintentional operation (errant operation).

To achieve the above problem, an X-ray fluoroscopic imaging apparatus according to the aspect of the present invention comprises: a table on which a subject is loaded, an imaging element that irradiates an X-ray to a subject and detects the X-ray that transmits the subject, and implements the X-ray fluoroscopy or the X-ray imaging; a shifting mechanism capable of shifting a relative location between the imaging element and the table; a motion-axis selection switch to select a motion-axis when shifting the above relative location; an operation element that comprises a plurality of direction switches respectively corresponding to a plurality of directions and is operative to receive an operation by which the above relative location shifts; a control element that subjects the above relative location to the predetermined motion-axis mode capable of shifting the above relative location relative to the selected motion-axis when the predetermined motion-axis is selected from the plurality of motion-axes using motion-axis selection switch, and in addition, controls shifting of the above relative location in the direction responding to the operative direction switch using the shifting mechanism when any one of the plurality of direction switches is operative in the predetermined motion-axis mode.

As set for the above, according to the aspect of the present invention, the X-ray fluoroscopic imaging apparatus comprises the control element that subjects the above relative location to the predetermined motion-axis mode capable of shifting the above relative location relative to the selected motion-axis when the predetermined motion-axis is selected from the plurality of motion-axes using motion-axis selection switch, and in addition, controls the shifting of the above relative location in the direction responding to the operative direction switch using the shifting mechanism when any one of the plurality of direction switches is operative in the predetermined motion-axis mode. Therefore, the motion-axis selection switch, which selects the motion-axis among a plurality of motion-axes, and a plurality of direction switches are combined, so that the plurality of direction switches can be applied to the plurality of the motion-axes at the same time. As a result, a number of switches can be cut compared to the case in which each direction switch is assigned to each one of the plurality of motion-axes, so that the size of the operation element can be avoided to be large and in addition, the location of each desired switch can be easily identified so that the operability thereof can be improved. In addition, the two-steps operation of operating the motion-axis selection switch to subject to the predetermined motion-axis mode and operating a plurality of direction switches must be first carried out to shift the relative location set forth above. As a result, when not in the predetermined motion-axis mode, even when the plurality of direction switches is operative, the relative location set forth above does not shift, so that an unintentional shift of the above relative location can be avoided.

With regard to the X-ray fluoroscopic imaging apparatus according to the aspect as set forth above, it is preferable that the predetermined motion-axis comprises a straight-line motion-axis mode that shifts the above relative location by straight line-shifting in the direction of the motion-axis along, the longitudinal direction of the table or the direction of the motion-axis along the transverse direction thereof, and a rotation motion-axis that rotate-shifts the above relative location by a rotation-shifting relative to the direction of the motion-axis along the longitudinal direction of the table or the direction of the motion-axis along the transverse direction thereof.

According to such structure, one straight-line motion-axis mode can achieve the shifting of the above relative location by the straight line-shifting relative to the two motion-axes, and one rotation motion-axis mode can achieve the shifting of the above relative location by the rotation-shifting relative to the two motion-axes. In addition, each motion-axis for the straight line-shifting and each motion-axis for the rotation-shifting are respectively combined to make one unit, so that an increase of the number of modes can be suppressed, and consequently, the operability can be further improved.

With regard to the motion-axis mode set forth above that comprises, the straight-line motion-axis mode and the rotation motion-axis mode.

It is preferable that the plurality of direction switches comprises 4 switches, i.e., up-, down-, right-, and left-direction switches, and either one switch pair of up-and-down direction switch pair or right-and-left direction, switch pair shifts the above relative location by the straight line-shifting relative to the motion-axis direction along the longitudinal direction, and the other switch pair of the direction switches shifts the above relative location by the line-shifting in the motion-axis direction along the transverse direction set forth above, and relative to the rotation motion-axis mode, either one switch pair of up-and-down direction switch pair or right-and-left direction switch pair shifts the above relative location by the rotation-shifting relative to the motion-axis along the longitudinal direction, and the other switch pair of the direction switches shifts the above relative location by the rotation-shifting relative to the motion-axis direction along the transverse direction set forth above. According to such structure, the operation of 4 switches, i.e., for up, down, right, and left directions, can, facilitate the recognition by the user to which direction the shifting takes place relative to each motion-axis mode.

With regard to the X-ray fluoroscopic imaging apparatus according to the aspect as set forth above, it is preferable that the shifting of the above relative location is carried out by shifting the table relative to the imaging element. Now, with regard to the X-ray fluoroscopic imaging apparatus, the operation tool having a plurality of direction switches is more often applied to the case in which the table shifts compared to the case in which the imaging system shifts. Therefore, according to the aspect of the present invention, the aspect, in which the motion-axis selection switch and a plurality of direction switches are combined so that the plurality of direction switches can be applied relative to the plurality of the motion-axes at the same time, is particularly effective when the table shifts relative to the imaging system.

With regard to the X-ray fluoroscopic imaging apparatus according to the aspect as set forth above, it is preferable that the control element cancels the predetermined motion-axis mode when no operation takes place for the predetermined time period following subjecting to the predetermined motion-axis mode. According to such structure, even when the motion-axis selection switch is erroneously operative to subject to the predetermined motion-axis mode, the predetermined motion-axis mode can be canceled after passing a constant time period. As a result, the state in which the above relative location can shift is just being kept for a constant time period by operating a plurality of the direction switches, so that an unintentional shift of the above relative location can be further strongly avoided.

With regard to the X-ray fluoroscopic imaging apparatus according to the aspect as set forth above, it is preferable that the control element lights up or blinks either one of the motion-axis selection switch or a plurality of the direction switches or both under the aspect in which a plurality of motion-axis modes is distinguishable with one another. According to such structure, the present motion-axis mode can be easily comprehended by the eyes.

With regard to the aspect in which the above plurality of the motion-axis modes lights up or blink as distinguishable one another, it is preferable that the control element lights up or blinks either one of the motion-axis selection switch or a plurality of the direction switches or both under the aspect in which each of motion-axis modes lights up or blinks in a different color to one another. According to such aspect, the present motion-axis mode can be easily comprehended by the eyes.

With regard to the X-ray fluoroscopic imaging apparatus according to the aspect as set forth above, it is preferable that a plurality of the motion-axis selection switches is installed every predetermined motion-axis mode and at least one of a figure and a letter corresponding to the predetermined motion-axis mode is displayed. Such structure can facilitate to select the motion-axis mode and to comprehend the present motion-axis mode.

It is preferable that the X-ray fluoroscopic imaging apparatus according to the aspect as set forth above further comprises a switch that switches the state, in which the above relative location is manually shiftable, and the state, in which the above relative location is shiftable by that the control element controls the shifting mechanism based on the operations of the motion-axis selection switch and the direction switch. According to such aspect, the manual operation and the operation that is using the motion-axis selection switch and the direction switch cannot be operative at the same time. As a result, for example, during the manual operation, the unintentional shifting of the above relative location due to the errant operation of the motion-axis selection switch and the direction can be avoided.

With regard to the X-ray fluoroscopic imaging apparatus according to the aspect as set forth above, it is preferable that the shifting of the above relative location using a plurality of direction switches is carried out just only while the plurality of direction switches is being operative. According to such aspect, the shifting of the above relative location is carried out just only while the plurality of direction switches is being operative, so that such aspect can facilitate to shift the above relative location only within the intended shifting amount.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 10A, 10B are schematic views illustrating the straight line-shifting of the imaging element relative to the X-ray fluoroscopic imaging apparatus according to the aspect of the Embodiment 2 of the present invention.

DETAILED DESCRIPTION OF THE PREFERRED EMBODIMENTS

Figure 1A:
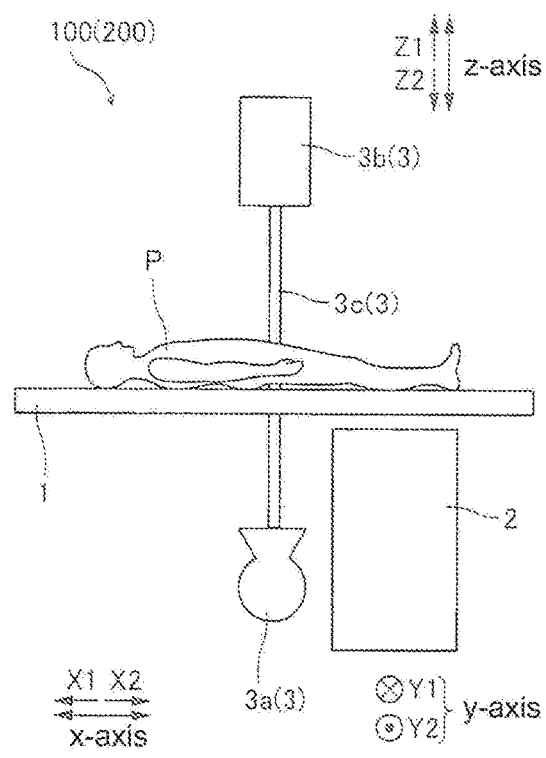
FIG. 1A, 1B are schematic views illustrating a side view and a front view denoting an entire structure of an X-ray fluoroscopic imaging apparatus according to the aspect of the Embodiments 1, 2 of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, and, as will be understood by one of skill in the computer engineering and computer science arts, a "computer-type system" includes an input device for receiving data, an output device for outputting data in tangible form (e.g. data transmission, data display, printing or displaying on a computer screen, data storing, data manipulation, data calculation, etc.), a memory for storing data as well as computer code, and a processor (of any kind) for executing computer code wherein said computer code resident in said memory (permanent or transitory) will physically cause said microprocessor to read-in data via said input device, process said data within said processor(s) and output said processed data via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray fluoroscopic imaging apparatus arts, devices, computer and operational controls and technologies of radiographic and fluoroscopic devices and all their sub components, including various circuits and combinations of circuits without departing from the scope and spirit of the present invention.

The inventor sets forth specific Embodiments of the present invention based on the following FIGs.

Embodiment 1

Referring to FIG. 1A-FIG. 3, the inventor illustrates the system of the X-ray fluoroscopic imaging apparatus 100 according to the aspect of the Embodiment 1 of the present invention.

[System of an X-Ray Fluoroscopic Imaging Apparatus]

Figure 1B:
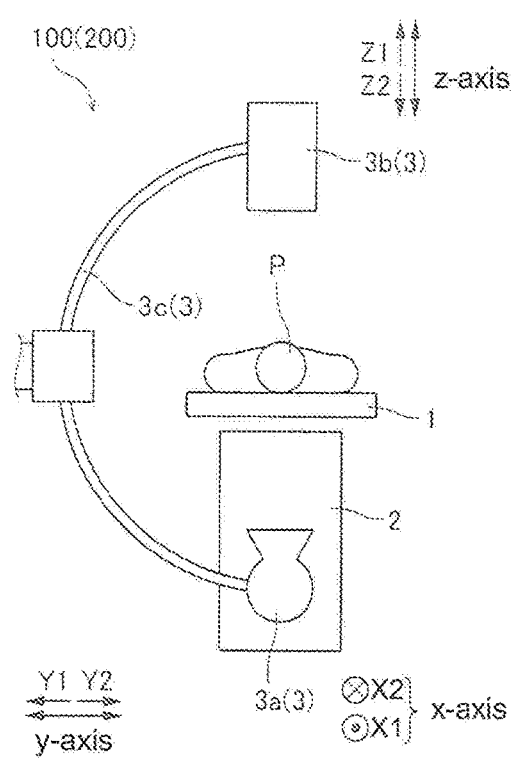

Referring to FIG. 1A, 1B, the X-ray fluoroscopic imaging apparatus 100 according to the aspect of the Embodiment 1 comprises a table 1 that loads a subject P, an examination table pedestal 2 that supports the table 1, and an imaging element 3 that images the subject P.

The plan view of the table 1 looks like a rectangular flat board. The subject P is lying down on the table 1 as the direction of the subject P from the head to the toe is along the long-side of the rectangle (the longitudinal direction of the table 1) and the right-and-left direction of the subject P is along the short-side of the rectangle (transverse direction of the table 1). In addition, in the present specification, the longitudinal direction of the table 1 is the x-axis direction, the transverse direction of the table 1 is the y-axis direction, the orthogonal direction to the x-axis direction and the y-axis direction is the z-axis direction.

The examination table pedestal 2 is in-place below the table 1 and connected thereto through such as a shifting mechanism 5 (referring to FIG. 2) that can shift the table 1 supported thereby.

An imaging element 3 comprises an X-ray, source, an X-ray tube device 3a in-place in the one-side of the table 1, an X-ray image receiver 3b in-place in the other side of the table 1, and an C-shaped arm 3c supporting the X-ray tube device 3a and the X-ray image receiver 3b.

The X-ray tube device 3a comprises the X-ray source and is capable of irradiating an X-ray when an electric voltage is added by an X-ray tube driving element, not shown in FIG. The X-ray image receiver 3b comprises an FPD (flat panel detector) and is capable of detecting the X-ray. Therefore, the X-ray fluoroscopic imaging apparatus 100 is capable of irradiating an X-ray from the X-ray tube device 3a under the state in which the subject P is lying down on the table 1, detecting the X-ray, which transmits the subject P, by the X-ray image receiver 3b, and implementing the X-ray fluoroscopy and the X-ray imaging relative to the subject P.

Figure 2:
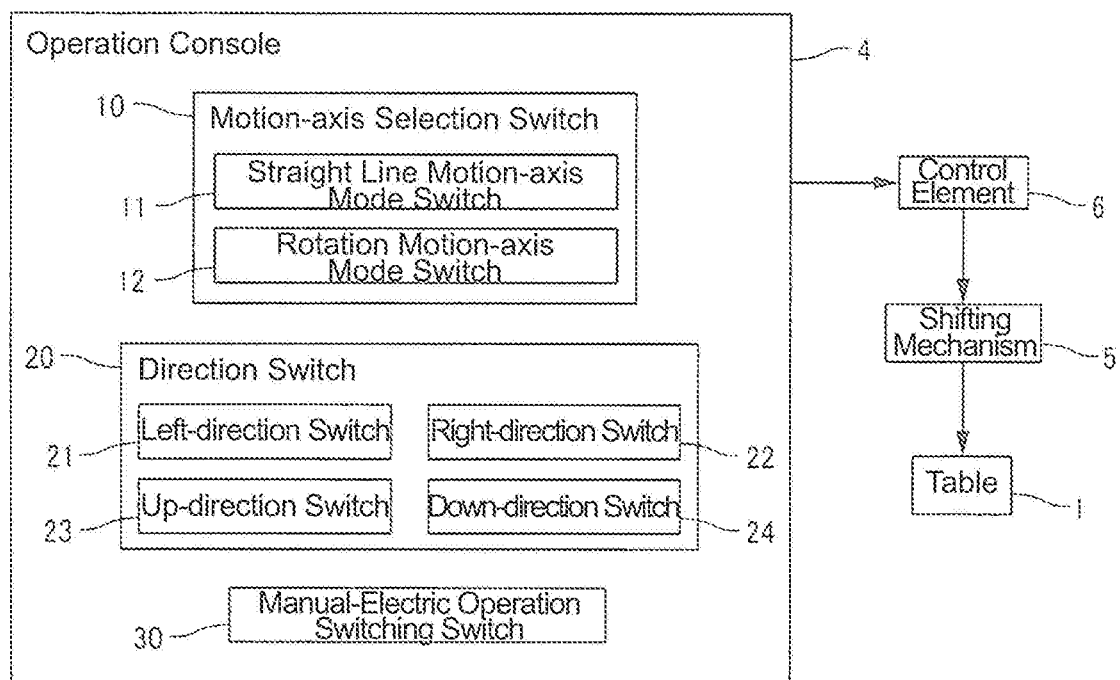
FIG. 2 is a block diagram illustrating an entire structure of the X-ray fluoroscopic imaging apparatus according to the aspect of the Embodiment 1 of the present invention.
Figure 3:
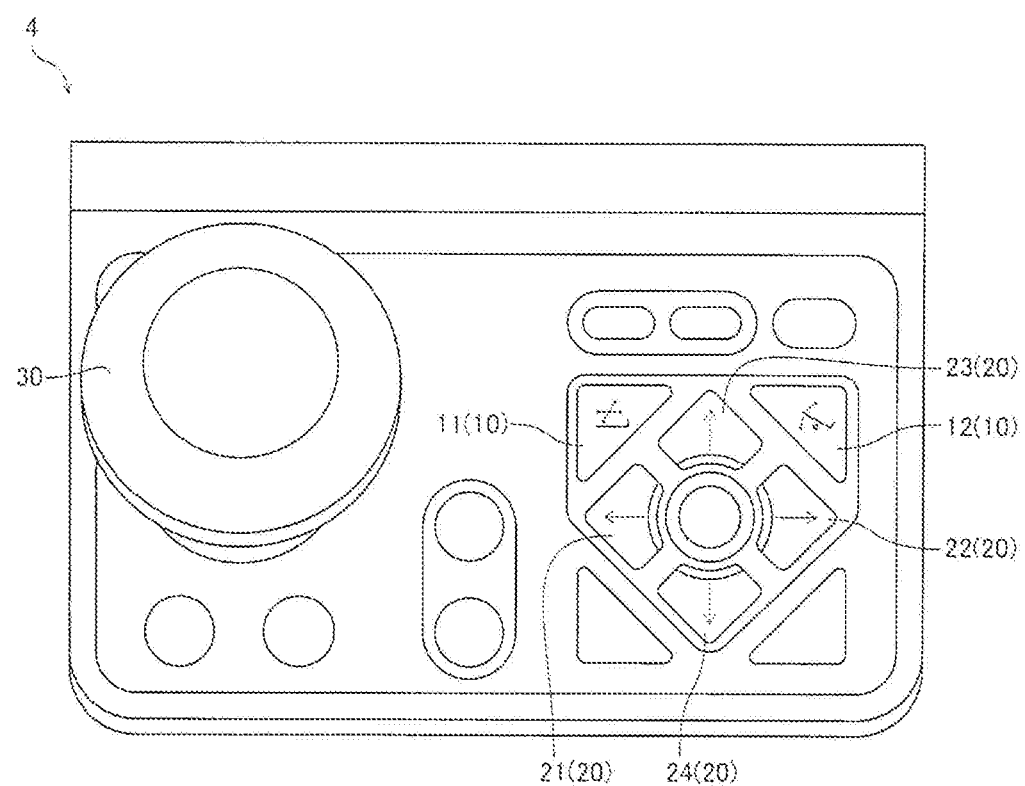
FIG. 3 is a schematic view illustrating an operation console of the X-ray fluoroscopic imaging apparatus according to the aspect of the Embodiment 1 of the present invention.

Referring to FIG. 2, FIG. 3, the X-ray fluoroscopic imaging apparatus 100 further comprises an operation console 4 that, receives the operation that shifts the table 1, the shifting mechanism 5 capable of shifting the table 1, and a control element 6 that controls shifting of the table 1 by the shifting mechanism 5. In addition, the operation console 4 is an example of the operation element in the claims.

The operation console 4 comprises a motion-axis selection switch 10 that selects the motion-axis A (referring to FIG. 7B) when the table 1 shifts, a direction switch 20 that responds to a plurality of directions, and a manual-electric operation switching switch 30 that switches between the shiftable state of the table 1 by the electric operation and the shiftable state of the table 1 manually. In addition, the manual-electric operation switching switch 30 is an example of the switching switch in the claims.

The motion-axis selection switch 10 comprises a straight-line motion-axis mode switch 11 to subject to the straight-line motion-axis mode and the rotation motion-axis mode switch 12 to subject to the rotation motion-axis mode. The straight-line motion-axis mode switch 11 and the rotation motion-axis mode switch 12 switch the motion-axis mode every time when pressed down. For example, when not subject to any motion-axis mode and given an arbitrary motion-axis selection switch 10 is pressed down, the motion-axis mode is subjected to the motion-axis mode corresponding to the motion-axis selection switch 10 that is pressed down. In addition, when subject to a motion-axis mode and given the motion-axis selection switch 10 corresponding to the different motion-axis mode from the present motion-axis mode is pressed down, the motion-axis mode is subjected to the motion-axis mode corresponding to the motion-axis selection switch 10 that is pressed down.

In addition, with regard to the X-ray fluoroscopic imaging apparatus 100 according to the aspect of the Embodiment 1, no operation is implemented for continuous ten seconds following being subjected to any motion-axis mode, the motion-axis mode is canceled. In addition, when subject to any motion-axis mode, the corresponding motion-axis selection switch 10 puts to light up as in the aspect in which a plurality of motion-axis modes is distinguishable with one another. Specifically, when subject to any motion-axis mode, the corresponding motion-axis selection switch 10 puts to light up with a different color according to each motion-axis mode (referring to FIG. 4A-FIG. 7B). In addition, the straight-line motion-axis mode switch 11 and the rotation motion-axis mode switch 12 have a distinguishable figure that denotes the motion-axis selection switch 10 for respectively the straight-line motion-axis mode and the rotation motion-axis mode.

The direction switch 20 comprises 4 switches, i.e., the left-direction switch 21, the right-direction switch 22, the up-direction switch 23, and the down-direction switch 24. Each sign (arrow) indicating each direction is displayed on the left-direction switch 21, the right-direction switch 22, the up-direction (toward head) switch 23, and the down-direction (toward toe) switch 24. While subject to either straight-line motion-axis mode or rotation motion-axis mode, the direction switch 20 shifts the table 1 in the direction corresponding to each direction switch 20 only for the period in which each switch is being pressed down by continuously pressing down (operation) each direction switch 20. In addition, when subject to either motion-axis mode, the direction switch 20 puts to light up with the same color as the motion-axis selection switch 10 (referring to FIG. 4A-FIG. 7B).

The manual-electric operation switching switch 30 is capable of switching between the state, in which the table 1 is shiftable based on the operation using the motion-axis selection switch 10 and the direction switch 20, and the state, in which the table 1 is shiftable manually. The X-ray fluoroscopic imaging apparatus 100 according to the Embodiment 1 is capable of switching the method that shifts the table 1 between the manual operation and the electric operation every time when the manual-electric operation switching switch 30 is pressed down.

The shifting mechanism 5 is capable of shifting the table 1 relative to the imaging element 3 (and the examination table pedestal 2). Specifically, the shifting mechanism 5 enables the table 1 to shift in the straight-line relative to the motion-axis AX (referring to FIG. 4A, 4B) along the x-axis direction and the motion-axis AY along the y-axis direction (referring to FIG. 5A, 5B), and in addition, to rotate-shift relative to the motion-axis A2 (referring to FIG. 7A, 7B) along the x-axis direction and the motion-axis A1 (referring to FIG. 6A, 6B) along the y-axis direction. The inventor sets forth the detail of the motion-axis A (AX, AY, A1, A2) later.

The control element 6 is a computer comprising a CPU (central processing unit), ROM (read only memory) and RAM (random access memory) and so forth. The control element 6 controls to shift the table 1 based on the operation that the operation console 4 receives.

With regard to the X-ray fluoroscopic imaging apparatus 100 according to the aspect as set forth above, the motion axis selection switch 10 is operative, so that the motion-axis mode changes from a plurality of the motion-axis A to the motion-axis mode by which the table 1 can be shifted relative to the arbitrary motion-axis A. And, a plurality of direction switches 20 is operative under the subject motion-axis mode, so that the table 1 can be shifted (i.e., the relative location between the imaging element 3 and the table shifts) in the direction corresponding to the operative direction switch 20.

(Detail of the Operation of the Operation Console and the Shifting of the Table)

Next, referring to FIG. 4A-FIG. 7B, the inventor sets forth the shifting of the table 1 based on the operation of the operation console 4 in detail.

Next, the inventor sets forth the rotation operation of the table 1. When subject to the straight-line motion-axis mode by pressing down the straight-line motion-axis mode switch 11, referring to FIG. 4A-FIG. 5B, the straight-line motion-axis mode switch 11 lights up with a blue color. In addition, for convenient sake relative to the FIG., the state in which the lighting in blue is illustrated as diagonal lines from top left to bottom right.

Figure 4A:
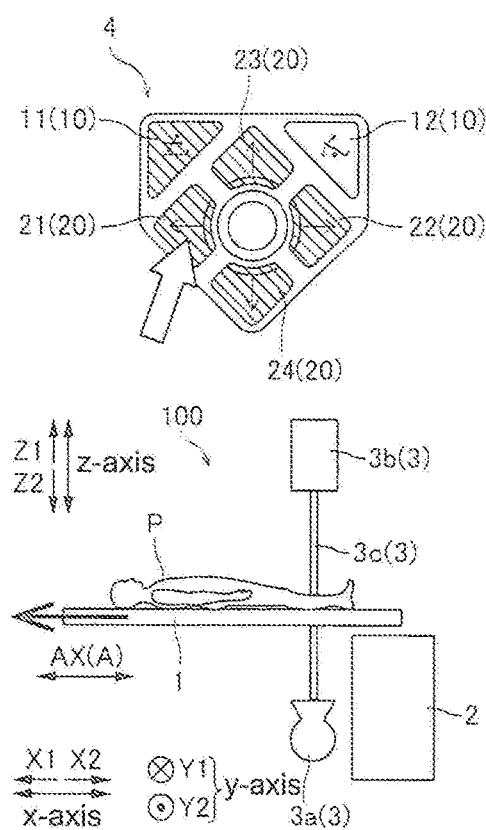
FIG. 4A, 4B are schematic views illustrating the straight line-shifting of the table relative to the X-ray fluoroscopic imaging apparatus according to the aspect of the Embodiment 1 of the present invention.
Figure 4B:
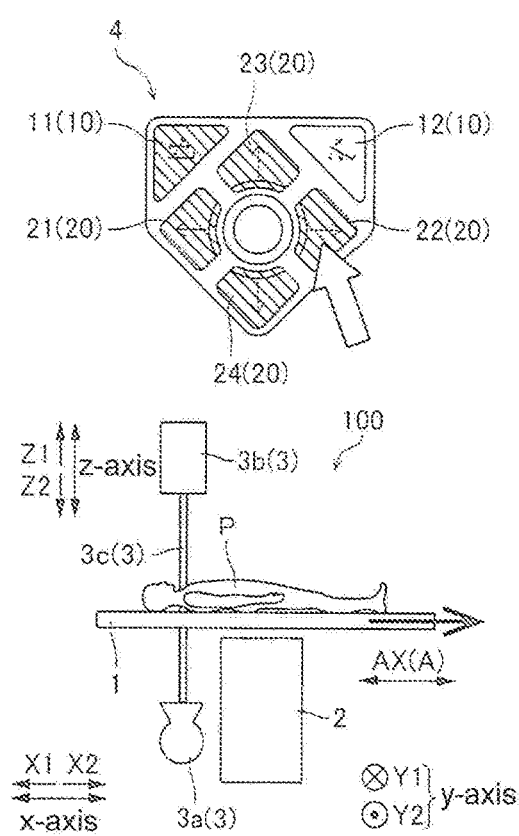

Referring to FIG. 4A, in the straight-line motion-axis mode, when the left-direction switch is continuously pressed down, the table 1 shifts along the straight-line in the X1 direction as long as the left-direction switch 21 is being pressed down. In addition, referring to FIG. 4B, in the straight-line motion-axis mode, when the right-direction switch is continuously pressed down, the table 1 shifts along the straight-line in the X2 direction as long as the right-direction switch 22 is being pressed down. Specifically, once the switch pair of the right-direction switch and left-direction switch is pressed down in the straight-line motion-axis mode, the table 1 shifts along the straight-line in the one side and the other side in the motion-axis AX direction along the x-axis direction. In addition, the aspect in which the direction switch 20 is pressed downs indicated by each thick arrow.

Figure 5A:
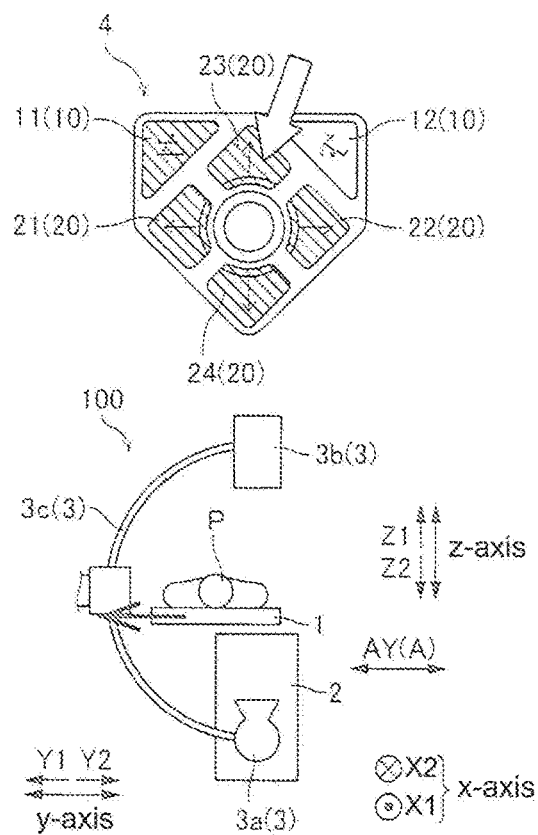
FIG. 5A, 5B are schematic views illustrating the alternative straight line-shifting of the table relative to the X-ray fluoroscopic imaging apparatus according to the aspect of the Embodiment 1 of the present invention.
Figure 5B:
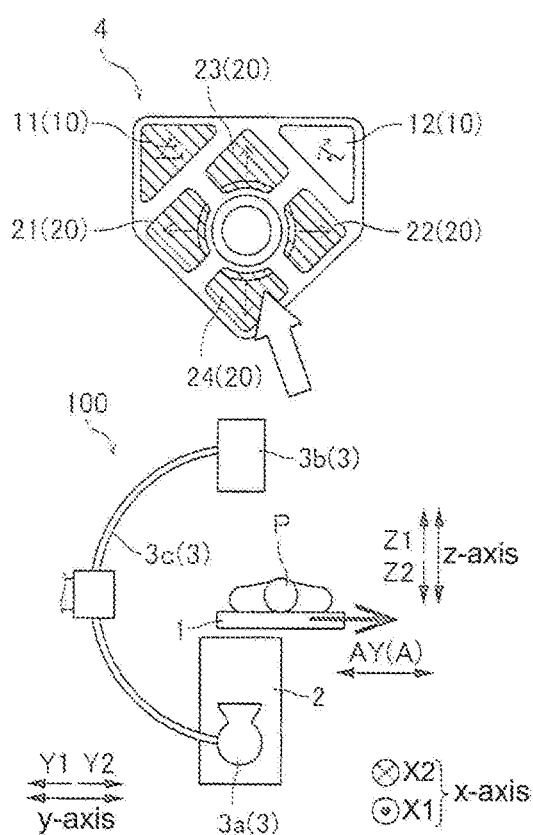

In addition, referring to FIG. 5A, in the straight-line motion-axis mode, when the up-direction switch is continuously pressed down, the table 1 shifts along the straight-line in the Y1 direction as long as the up-direction switch 23 is being pressed down. In addition, referring to FIG. 5B, in the straight-line motion-axis mode, when the down-direction switch is continuously pressed down, the table 1 shifts along the straight-line in the Y2 direction as long as the down-direction switch 24 is being pressed down. Specifically, once the switch pair of the up-direction switch and down direction switch is pressed down in the straight-line motion-axis mode, the table 1 shifts along the straight-line in the one side and the other side in the motion-axis AY direction along the y-axis direction.

As set forth above, the table 1 is shiftable along one of the straight lines in the motion-axis AX direction along the longitudinal direction (x-axis direction) of the table 1, and in the motion-axis AY direction along the transverse direction (y-axis direction), in the straight-line motion-axis mode. Specifically, the straight-line shifting of the table 1 relative to the two motion-axes AX, AY can be achieved in just one straight-line motion-axis mode. In addition, the straight-line shifting along the direction of the motion-axis AX is operative by the left-direction switch 21 and the right-direction switch 22, and the straight-line shifting along the direction of the motion-axis AY is operative by the up-direction switch 23 and the down-direction switch 24, so that the direction switch 20 can be deemed consisting of a switch pair of the right-and-left switch and the up-and-down switch.

Next, the inventor sets forth the rotation operation of the table 1. When subject to the rotation motion-axis mode by pressing down the rotation line motion-axis mode switch 12, referring to FIG. 6A-FIG. 7B, the rotation motion-axis mode switch 12 lights up in a green color (different from the blue color in the straight-line motion-axis mode). In addition, for the convenient sake relative to the FIG., the state in which the lighting in green is illustrated as diagonal lines from top right to bottom left.

Figure 6A:
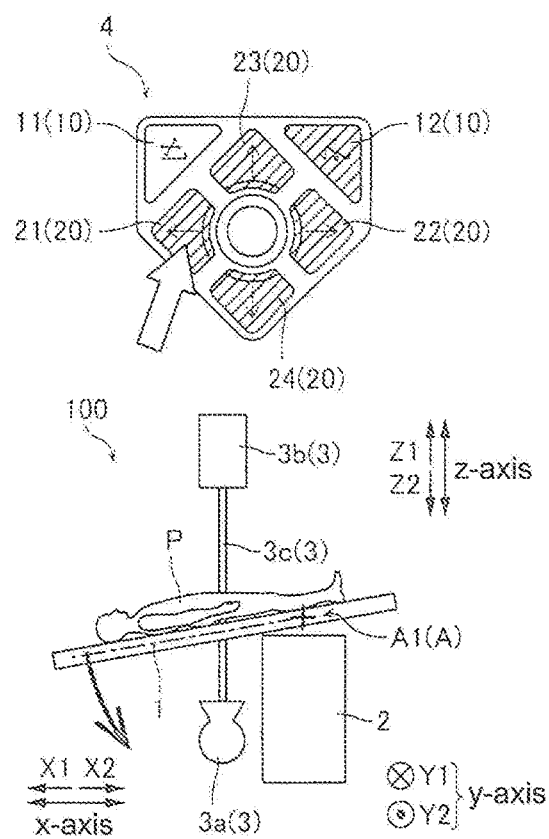
FIG. 6A, 6B are schematic views illustrating the rotation-shifting of the table relative to the X-ray fluoroscopic imaging apparatus according to the aspect of the Embodiment 1 of the present invention.
Figure 6B:
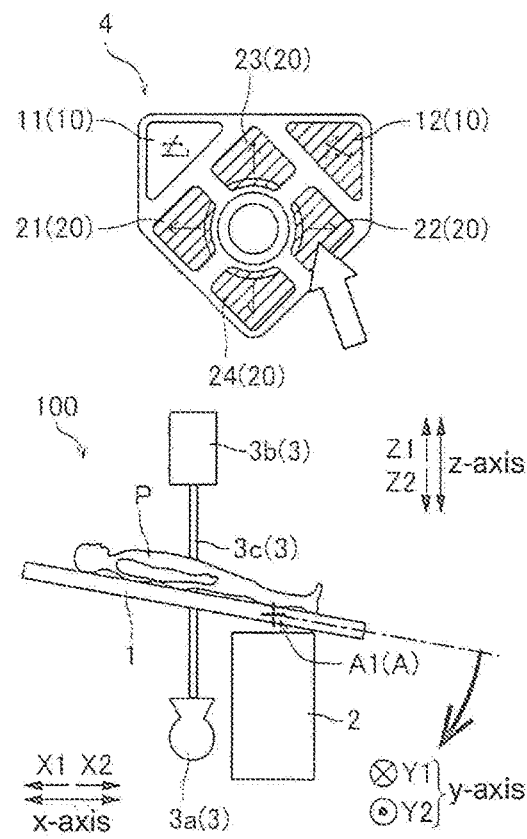

Referring to FIG. 6A, in the rotation motion-axis mode, when the left-direction switch 21 is continuously pressed down, the table 1 rotate-shifts counterclockwise viewing from the Y2 direction relative to the motion-axis A1 along the y-axis as long as the left-direction switch 21 is being pressed down. Referring to FIG. 6B, in the rotation motion-axis triode, when the right-direction switch 22 is continuously being pressed down, the table 1 rotate-shifts clockwise viewing from the Y2 direction relative to the motion-axis A1 along the y-axis as long as the left-direction switch 22 is being pressed down. Specifically, once the switch pair of the right-direction switch and left-direction switch is pressed down in the rotation motion-axis mode, the table 1 rotates in the one side and the other side relative to the motion-axis A1 direction along the y-axis direction. In addition, according to the aspect of the Embodiment 1, the motion-axis A1 is in-place above the examination table pedestal 2 in the z-axis direction and in addition, in-lace approximately at the same height as the height of the table 1.

Figure 7A:
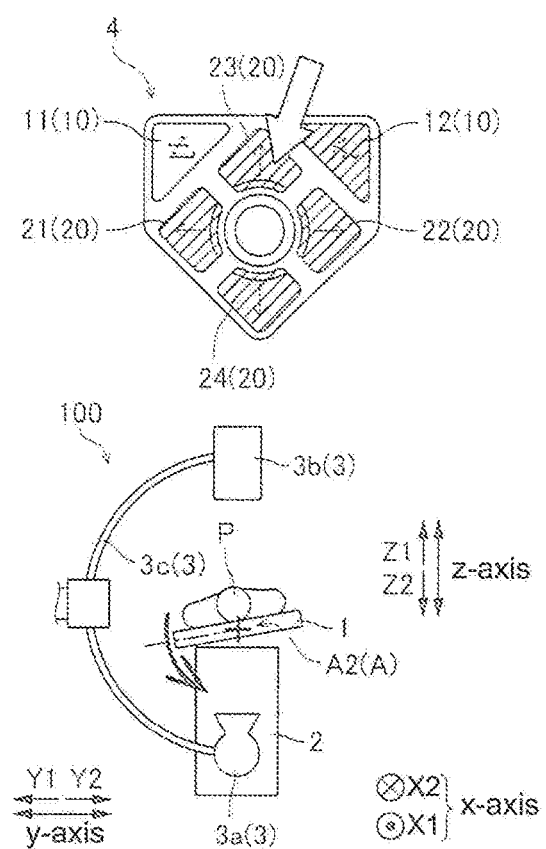
FIG. 7A, 7B are schematic views illustrating the alternative rotation-shifting of the table relative to the X-ray fluoroscopic imaging apparatus according to the aspect of the Embodiment 1 of the present invention.
Figure 7B:
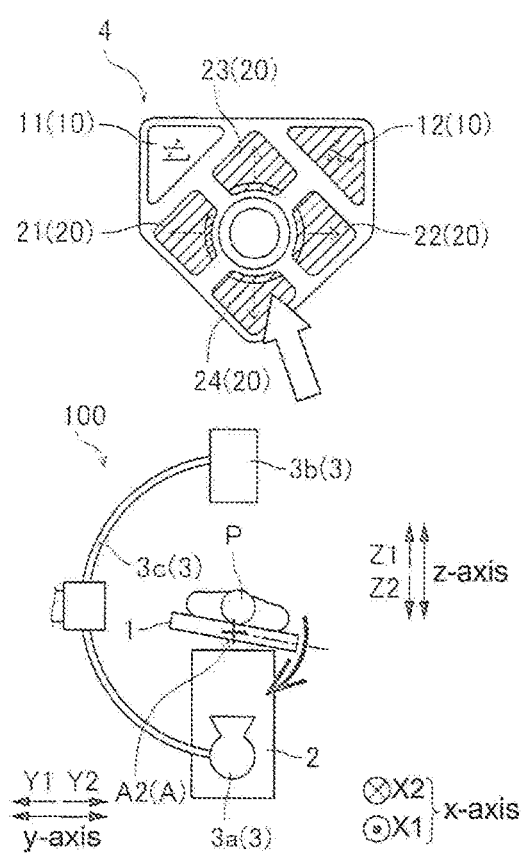

In addition, referring to FIG. 7A, in the rotation motion-axis mode, when the up-direction switch 23 is continuously pressed down, the table 1 rotate-shifts counterclockwise viewing from the X1 direction relative to the motion-axis A2 along the x-axis as long as the up-direction switch 23 is being pressed down. In addition, referring to FIG. 7B, in the rotation motion-axis mode, when the down-direction switch 24 is continuously pressed down, the table 1 rotate-shifts clockwise viewing from the X1, direction relative to the motion-axis A2 along the x-axis as long as the down-direction switch 24 is being pressed down. Specifically, once the switch pair of the up-direction switch and down-direction switch is pressed down in the rotation motion-axis mode, the table 1 rotate-shifts in one side and the other side relative to the motion-axis A2 direction along the y-axis direction. In addition, according to the aspect of the Embodiment 1, the motion-axis A2 as the same as the motion-axis A1 is in-place above the examination table pedestal 2 in the z-axis direction and in addition, in-place approximately at the same height as the height of the table 1.

As set forth above, the table 1 can be rotate-shifted relative to the motion-axis A2 direction along the longitudinal direction (x-axis direction) of the table 1, and in the motion-axis A1 direction along the transverse direction (y-axis direction) thereof, in the rotation motion-axis mode. Specifically, the rotation of the table 1 relative to the two motion-axes A1, A2 can be achieved in just one rotation motion-axis mode. In addition, the rotation-shifting along the direction of the motion-axis A1 is operative by the left-direction switch 21 and the right-direction switch 22, and the rotation-shifting along the direction of the motion-axis A2 is operative by the up-direction switch 23 and the down-direction switch 24, so that the direction switch 20 can be deemed consisting of a switch pair of the right-and-left switch and the up-and-down switch as the same as in the case of the straight-line motion-axis mode.

(Effect According to the Aspect of the Embodiment 1)

The following effects can be obtained according to the aspect of the Embodiment 1.

According to the aspect of the Embodiment 1 as set forth above, the relative location between the imaging element 3 and the table 1 is subjected to the predetermined motion-axis mode capable of shifting relative to the selected motion-axis A when the predetermined motion-axis A is selected from the plurality of motion-axes A using motion-axis selection switch 10. Then, when any one of a plurality of direction switches 20 is operative in the predetermined motion-axis mode, the control element 6 control to shift the relative location between the imaging element 3 and the table 1 shifts by the shifting mechanism 5 in the direction corresponding to the operative direction switch 20. Therefore, the motion-axis selection switch 10, which selects the motion-axis A among a plurality of motion-axes A, and a plurality of direction switches 20 are combined, so that the plurality of direction switches 20 can be applied relative to the plurality of the motion-axes A at the same time. As a result, a number of switches can be cut compared to the case in which each direction switch 20 is assigned to each one of the plurality of motion-axes A, so that the size of the operation console 4 can be avoided to be large and in addition, the location of each desired switch can be easily identified so that the operability thereof can be improved. In addition, the two-steps operation comprising a step of operating the motion-axis selection switch 10 to subject to the predetermined motion-axis mode and a step of operating a plurality of direction switches 20 is carried out, so that the relative location between the imaging element 3 and the table 1 can shifts first. As a result, when not subject to the predetermined motion-axis mode, even when the plurality of direction switches 20 are operative, the relative location between the imaging element 3 and the table 1 does not shift, so that an unintentional shift of the relative location between the imaging, element 3 and the table 1 can be avoided.

In addition, according to the aspect of the Embodiment 1 set forth above, the control element 6 comprises the predetermined motion-axis mode consisting of the straight-line motion-axis mode that shifts the relative location between the imaging element 3 and the table 1 by the straight-line shifting in the motion-axis AX direction along the longitudinal direction of the table 1 or in the motion-axis AY direction along the transverse direction thereof, and the rotation motion-axis mode that shifts the relative location between the imaging element 3 and the table 1 by the rotation in the motion-axis A2 along the longitudinal direction of the table 1 or in the motion-axis A1 along the transverse direction thereof. Therefore, one straight-line motion-axis mode can achieve the shifting of the relative location between the imaging element 3 and the table 1 by the straight line-shifting relative to the two motion-axes AX, AY, and one rotation motion-axis mode can achieve the shifting of the above relative location between the imaging element 3 and the table 1 by the rotation-shifting relative to the two motion-axes A1, A2. In addition, each motion-axes AX, AY for the straight line-shifting and each motion-axes A1, A2 for the rotation-shifting are respectively combined to make one mode, so that an increase of the number of modes can be suppressed, and consequently, the operability can be further improved.

In addition, according to the aspect of the Embodiment 1 set forth above, a plurality of direction switches 20 comprises 4 switches, i.e., the up direction switch 23, the down-direction switch 24, the left-direction switch 21, the right-direction switch 22. Then, the control element 6 controls so that one switch pair of the left-direction switch 21 and the right-direction switch 22 among the direction switches 20 shifts the relative location between the imaging element 3 and the table 1 by the straight line-shifting relative to the motion-axis AX direction along the longitudinal direction of the table 1, and the switch pair of the up-direction switch 23 and the down-direction switch 24 shifts the relative location between the imaging element 3 and the table 1 by the straight line-shifting relative to the motion-axis AY direction along the transverse direction of the table 1. In addition, the control element 6 controls so that one switch pair of the left-direction switch 21 and the right-direction switch among the direction switches 20 shifts the relative location between the imaging element 3 and the table 1 by the rotation-shifting relative to the motion-axis A2 along the longitudinal direction of the table 1, and the switch pair of the up-direction switch 23 and the down-direction switch 24 shifts the relative location between the imaging element 3 and the table 1 by the rotation-shifting relative to the motion-axis A1 along the transverse direction of the table 1. Therefore, the operation of 4 switches, i.e., for up, down, right, and left directions, can facilitate the recognition by the user to which direction the shifting, takes place relative to each motion-axis mode.

In addition, according to the aspect of the Embodiment 1, as set forth above, the control element 6 controls so that the shifting of the relative location between the imaging element 3 and the table 1 is carried out by shifting the table 1 relative to the imaging element 3. Therefore, the aspect, in which the motion-axis selection switch 10 and a plurality of direction switches 20 are combined so that the plurality of direction switches 20 can be applied relative to the plurality of the motion-axes A at the same time, is particularly effective when the table 1 shifts relative to the imaging system 3.

According to the aspect of the Embodiment 1, as set forth above, the control element 6 cancels the predetermined motion-axis mode when no operation takes place for 10 seconds following being subjected to the predetermined motion-axis. Therefore, even when the motion-axis selection switch 10 is erroneously operative to subject to the predetermined motion-axis mode, the predetermined motion-axis mode can be canceled after passing 10 seconds. As a result, the state in which the relative location can shift is just being kept for only 10 seconds by operating a plurality of the direction switches 20, so that an unintentional shifting of the table 1 relative to the imaging element 3 can be further-strongly avoided.

According to the aspect of the Embodiment 1, as set forth above, the control element 6 lights up either the motion-axis selection switch 10 or a plurality of the direction switches 20 in the aspect in which a plurality of motion-axis modes is distinguishable with one another. Therefore, the present motion-axis mode can be easily comprehended by the eyes.

In addition, according to the aspect of the Embodiment 1, as set forth above, the control element 6 lights up both the motion-axis selection switch 10 and a plurality of the direction switches 20 with a different color relative to each motion-axis mode one another. Therefore, the present motion-axis mode can thither facilitate to comprehend by eyes.

In addition, according to the aspect of the Embodiment 1, as set forth above, a plurality of the motion-axis selection switches is installed every predetermined motion-axis mode and the figure corresponding to each predetermined motion-axis mode is displayed. Therefore, such aspect can facilitate to select the motion-axis mode and to comprehend the motion-axis mode.

In addition, according to the aspect of the Embodiment 1, as set forth above, the manual-electric operation switching switch 30 that switches the state, in which the relative location between the imaging element 3 and the table 1 is shiftable, and the state, in which the relative location between the imaging element 3 and the table 1 is shiftable by that the control element 6 controls the shifting mechanism 5 based on the operations of the motion-axis selection switch 10 and the direction switch 20 is further installed. According to such aspect, the manual operation and the operation that is using the motion-axis selection switch 10 and the direction switch 20 cannot be operative at the same time relative to shifting of the relative location between the imaging element 3 and the table 1. As a result, for example, during the manual operation, the unintentional shifting of the relative location between the imaging element 3 and the table 1 due to the errant operation of the motion-axis selection switch 10 and the direction switch 20 can be avoided.

In addition, according to the aspect of the Embodiment 1, as set forth above, the control element 6 controls so that the shifting of the relative location between the imaging element 3 and the table 1 can, be carried out only while a plurality of the direction switches are operative. According to such aspect, the shifting of the relative location between the imaging element 3 and the table 1 is carried out just only while the plurality of direction switches 20 are being operative, so that such aspect can facilitate to shift the relative location between the imaging element 3 and the table 1 only within the intended shifting amount.

Embodiment 2

Next, referring to FIG. 1, FIG. 8-FIG. 13B, the inventor illustrates the aspect of the Embodiment 2. The inventor sets forth that an X-ray fluoroscopic imaging apparatus 200 according to the aspect of the Embodiment 2, which is different from the X-ray fluoroscopic imaging apparatus 100 according to the aspect of the Embodiment 1, the shifting of the relative location between the imaging element 3 and the table 1 is carried out by shifting the imaging element 3. In addition, the same element as illustrated above according to the aspect of the Embodiment 1 is not set forth while providing the identical reference sign in FIGs.

[System of an X-Ray Fluoroscopic Imaging Apparatus]

Figure 8:
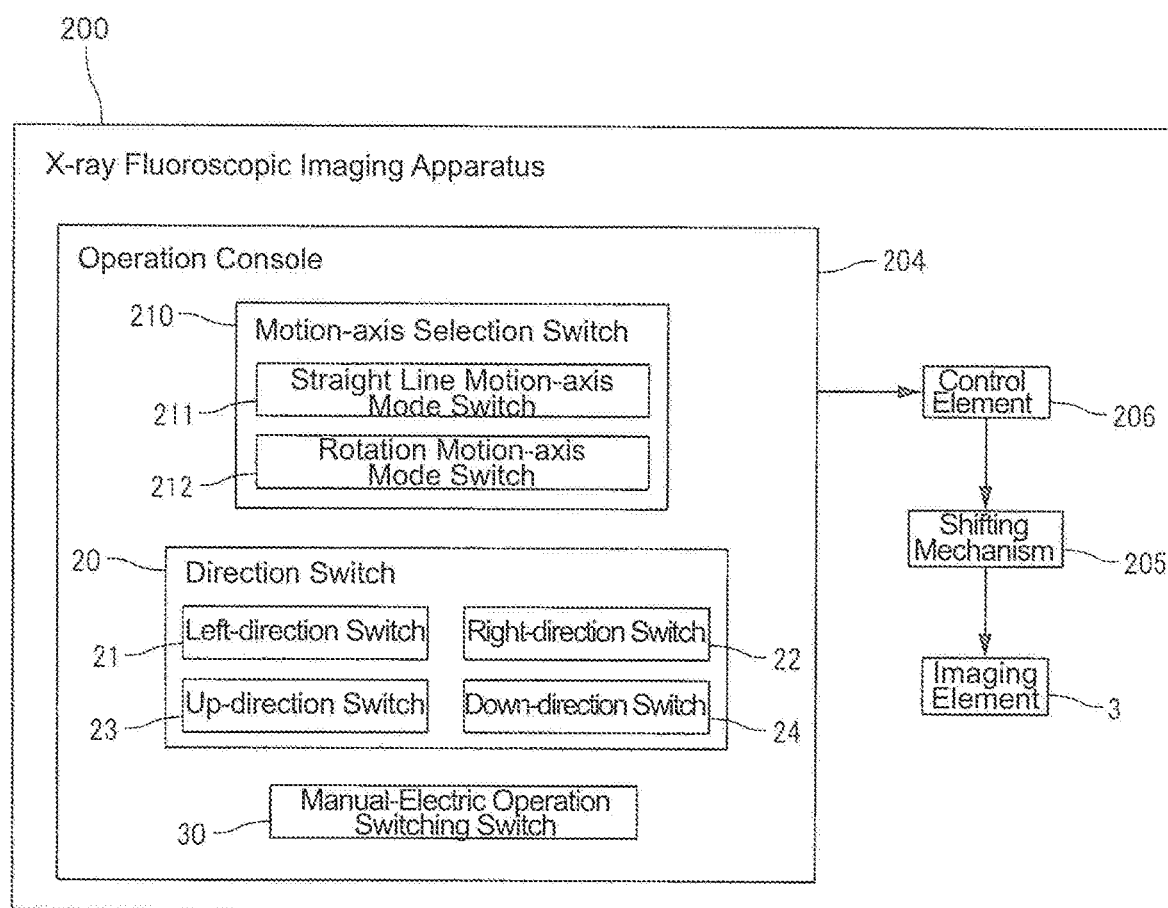
FIG. 8 is a block diagram illustrating an entire structure of the X-ray fluoroscopic imaging apparatus according to the aspect of the Embodiment 2 of the present invention.
Figure 9:
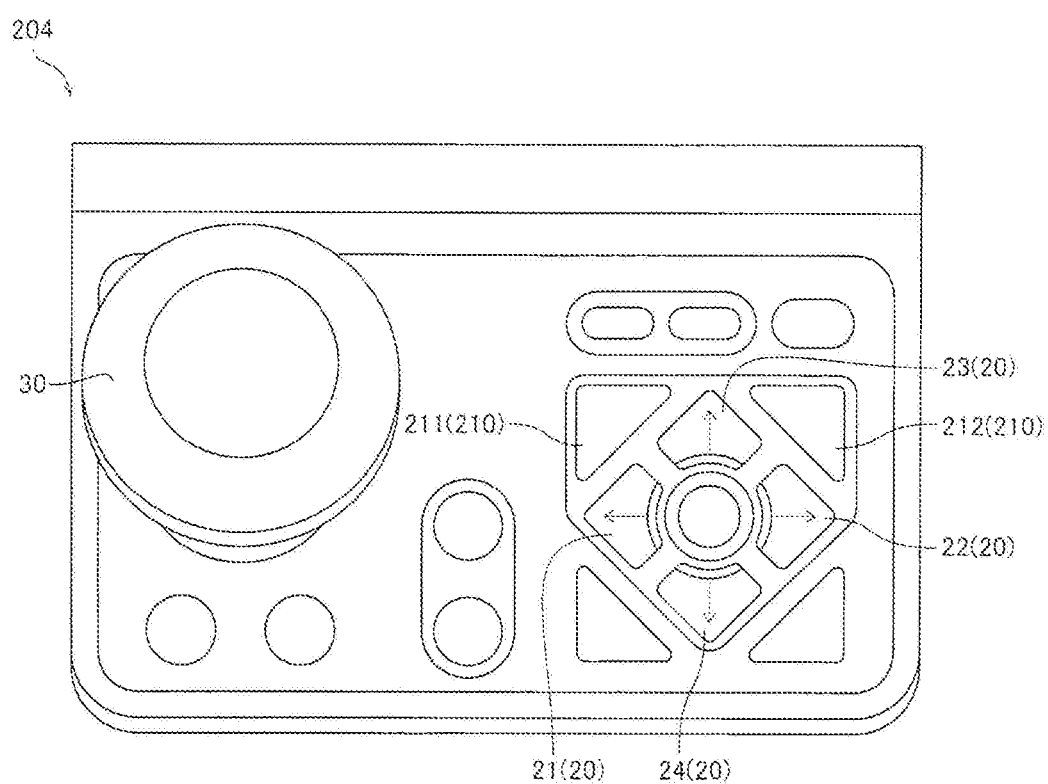
FIG. 9 is a schematic view illustrating an operation console of the X-ray fluoroscopic imaging, apparatus according to the aspect of the Embodiment 2 of the present invention.
Figure 11A:
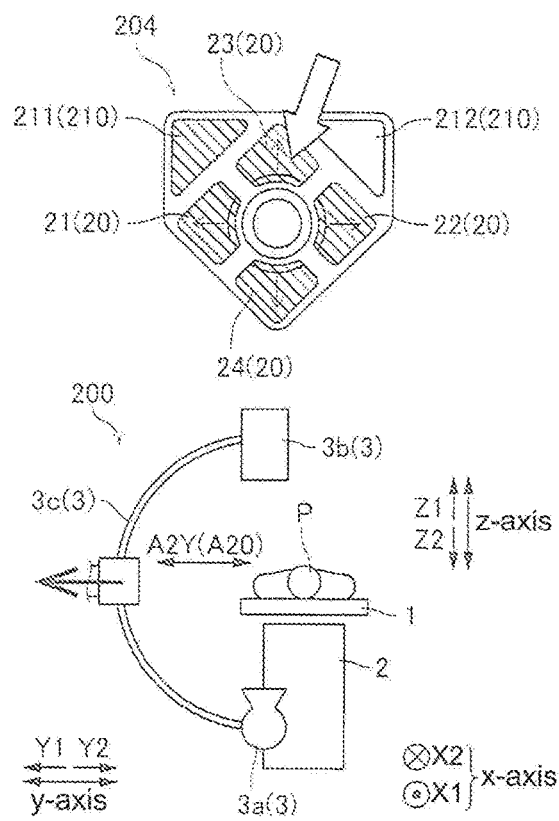
FIG. 11A, 11B are schematic views illustrating the alternative straight line-shifting of the imaging element relative to the X-ray fluoroscopic imaging apparatus according to the aspect of the Embodiment 2 of the present invention.
Figure 11B:
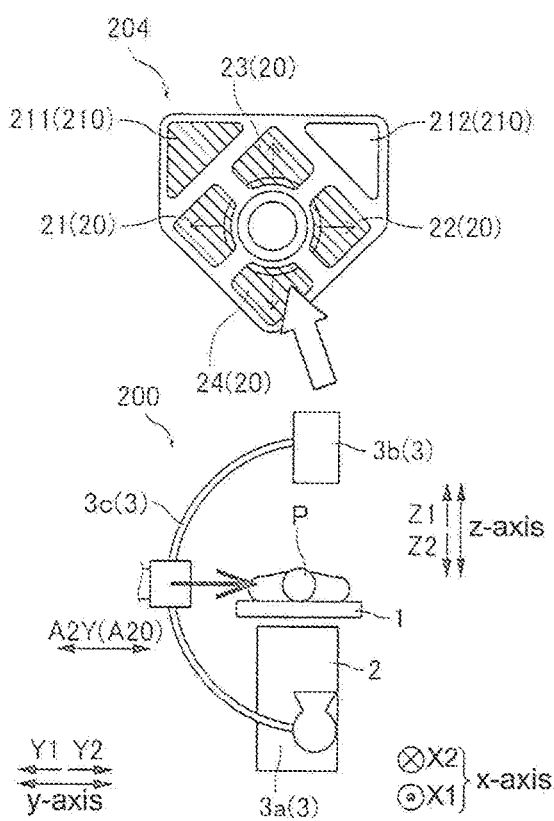

Referring to FIG. 8, FIG. 9, the X-ray fluoroscopic imaging apparatus 200 (referring to FIG. 1) comprises an operation console 204 that receives the operation that shifts the imaging element 3, the shifting mechanism 205 capable of shifting the imaging element 3, and a control element 206 that controls the shifting of the imaging element 3 by the shifting mechanism 5. In addition, the operation console 204 is an example of the operation, element in the claims.

The operation console 204 further comprises a motion-axis selection switch 210 that selects the motion-axis A20 (referring to FIG. 10A-FIG. 13B) when shifting the imaging element 3.

The motion-axis selection switch 210 comprises a straight-line motion-axis mode switch 211 to subject to the straight-line motion-axis mode and the rotation motion-axis mode switch 212 to subject to the rotation motion-axis mode. The straight-line motion-axis mode switch 211 and the rotation motion-axis mode switch 212 switch the motion-axis mode every time when pressed down, in addition, when subject to either motion-axis mode, the corresponding motion-axis selection switch 210 puts to light up with a different color according to each motion-axis mode (referring to FIG. 10A-FIG. 13B).

The shifting mechanism 205 is capable of shifting the imaging element 3 relative to the table 1 (and the examination table pedestal 2). Specifically, the shifting mechanism 205 enables the imaging element 3 to shift in the straight-line relative to the motion-axis A2X (referring to FIG. 10A, 10B) along the x-axis direction and the motion-axis A2Y along the y-axis direction (referring to FIG. 11A, 11B), and in addition, to rotate-shift relative to the motion-axis A22 (referring to FIG. 12A, 12B) along the x-axis direction and the motion-axis A21 (referring to FIG. 13A, 13B) along the y-axis direction. The inventor sets forth the detail of the motion-axes A20 (A2X, A2Y, A21, A22) later.

The control element 206 controls to shift the imaging element 3 based on the operation that the operation console 204 receives.

With regard to the X-ray fluoroscopic imaging apparatus 200 according to the aspect as set forth above, the motion-axis selection switch 210 is operative, so that the motion-axis mode changes from a plurality of the motion-axis A20 to the motion-axis mode by which the imaging element 3 can be shifted relative to the arbitrary motion-axis A20. And a plurality of direction switches 20 is operative under the subject motion-axis mode, so that the imaging element 3 can be shifted (i.e., the relative location between the imaging element 3 and the table 1 shifts) in the direction corresponding to the operative direction switch 20.

(Detail of the Operation of the Operation Console and the Shifting of the Imaging Element)

Next, referring to FIG. 10A-FIG. 13B, the inventor sets forth the shifting of the imaging element 3 based on the operation of the operation console 204 in detail.

Next, the inventor sets forth the straight-line operation of the imaging element 3. When subject to the straight-line motion-axis mode by pressing down the straight-line motion-axis mode switch 211, referring to FIG. 10A-FIG. 11B, the straight-line motion-axis mode switch 211 lights up in a blue color.

Referring to FIG. 10A, in the straight-line motion-axis mode, when the left-direction switch 21 is continuously pressed down, the imaging element 3 shifts along the straight-line in the X1 direction as long as the left-direction switch 21 is being pressed down. In addition, referring to FIG. 10B, in the straight-line motion-axis mode, when the right-direction switch 22 is continuously pressed down, the imaging element 3 shifts along the straight-line in the X2 direction as long as the right-direction switch 22 is being pressed down. Specifically, once the switch pair of the right-direction switch and left-direction switch is pressed down in the straight-line motion-axis mode, the imaging element 3 shifts along the straight-line in the one side and the other side in the motion-axis A2X direction along the x-axis direction.

In addition, referring to FIG. 10A, in the straight-line motion-axis mode, when the up-direction switch 23 is continuously pressed down, the imaging element 3 shifts along the straight-line in the Y1 direction as long as the up-direction switch 23 is being pressed down. In addition, referring to FIG. 10B, in the straight-line motion-axis mode, when the up-direction switch 23 is continuously pressed down, the imaging element 3 shifts along the straight-line in the Y2 direction as long as the down-direction switch 24 is being pressed down. Specifically, once the switch pair of the up-direction switch and down-direction switch is pressed down in the straight-line motion-axis mode, the imaging element 3 shifts along the straight-line in the one side and the other side in the motion-axis A2Y direction along the y-axis direction.

As set forth above, the imaging element 3 is shiftable along one of the straight lines in the motion-axis A2X direction along the longitudinal direction (x-axis direction) of the table 1, and in the motion-axis A2Y direction along the transverse direction (y-axis direction) thereof, in the straight-line motion-axis mode. Specifically, the straight-line shifting of the imaging element 3 relative to the two motion-axes A2X, A2Y can be achieved in just one straight-line motion-axis mode in addition, the straight-line shifting along the direction of the motion-axis A2X is operative by the left-direction switch 21 and the right-direction switch 22, and the straight-line shifting along the direction of the motion-axis A2Y is operative by the up-direction switch 23 and the down-direction switch 24, so that the direction switch 20 can be deemed consisting of a switch pair of the right-direction switch, and left-direction switch, or the up-direction switch and down-direction switch.

Next, the inventor sets forth the rotation operation of the imaging element 3. When subject to the rotation motion-axis mode by pressing down the rotation motion-axis mode switch 212, referring to FIG. 12A-FIG. 13B, the straight-line motion-axis mode switch 212 lights up in a green color.

Figure 12A:
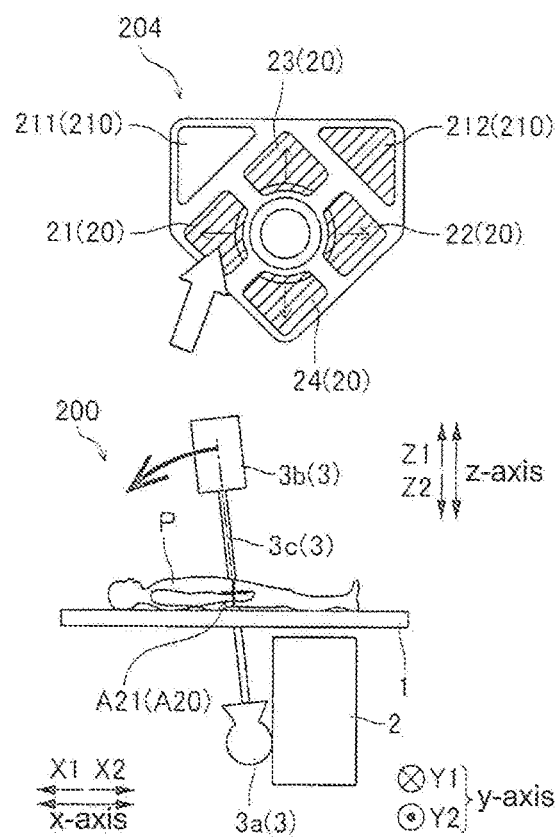
FIG. 12A, 12B are schematic views illustrating the rotation-shifting of the imaging element relative to the X-ray fluoroscopic imaging apparatus according to the aspect of the Embodiment 2 of the present invention.
Figure 12B:
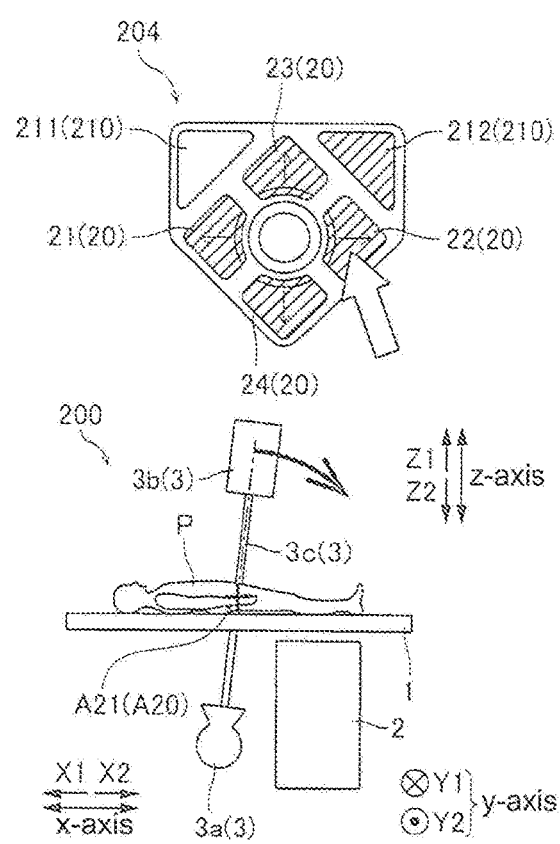

Referring to FIG. 12A, in the rotation motion-axis mode, when the left-direction switch 21 is continuously pressed down, the imaging element 3 rotate-shifts counterclockwise viewing from the Y2 direction relative to the motion-axis A21 along the y-axis as long as the left-direction switch 21 is being pressed down. Referring to FIG. 12B, in the rotation motion-axis mode, when the right-direction switch 22 is continuously pressed down, the imaging element 3 rotate-shifts clockwise viewing from the Y2 direction relative to the motion-axis A21 along the y-axis as long as the left-direction switch 22 is being pressed down. Specifically, once the switch pair of the right-direction switch and left-direction switch is pressed down in the rotation motion-axis mode, the imaging element 3 rotates in one side and the other side relative to the motion-axis A21 direction along the y-axis direction.

Figure 13A:
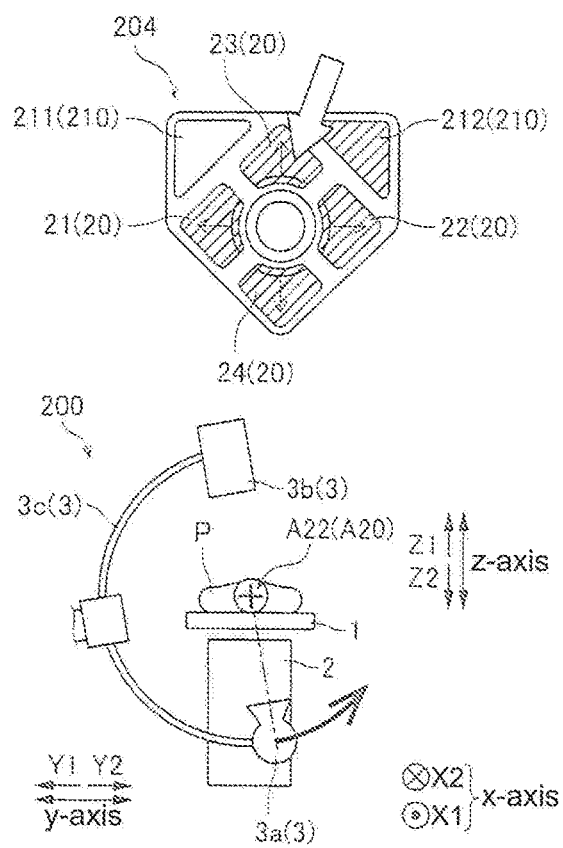
FIG. 13A, 13B are schematic views illustrating the alternative rotation-shifting of the imaging element relative to the X-ray fluoroscopic imaging apparatus according to the aspect of the Embodiment 2 of the present invention.
Figure 13B:
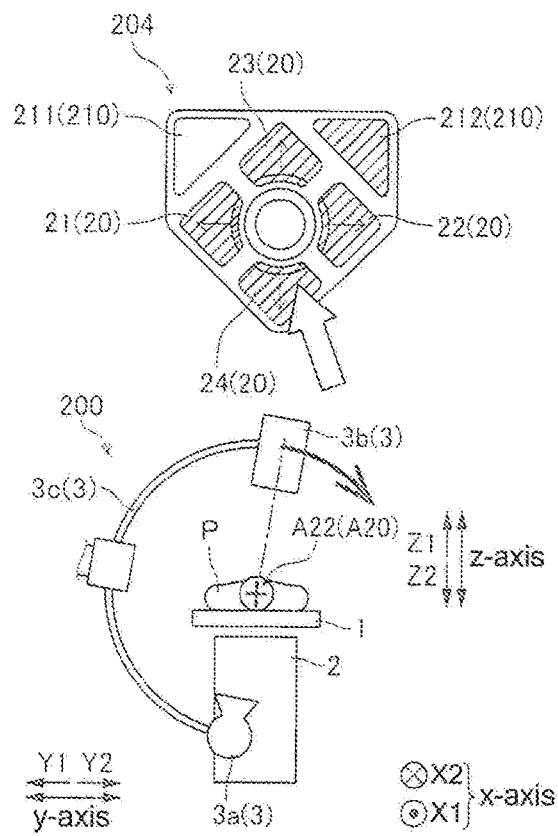

In addition, referring to FIG. 13A, the imaging element 3 rotate-shifts counterclockwise viewing from the X1 direction relative to the motion-axis A22 along the x-axis as long as the up-direction switch 23 is being pressed down when the up-direction switch 23 is continuously being pressed down in the rotation motion-axis mode. In addition, referring to FIG. 13B, the imaging element 3 rotate-shifts clockwise viewing from the X1 direction relative to the motion-axis A22 along the x-axis as long as the down-direction switch 24 is being pressed down when the down-direction switch 24 is continuously being pressed down in the rotation motion-axis mode. Specifically, once the switch pair of the up-direction switch and down-direction switch is pressed down in the rotation motion-axis mode, the imaging element 3 rotate-shifts in one side or the other side relative to the motion-axis A22 direction along the x-axis direction.

As set forth above, the imaging element 3 is rotatable relative to the motion-axis A22 direction along the longitudinal direction (x-axis direction) of the table 1, and in the motion-axis A21 direction along the transverse direction (y-axis direction) thereof, in the rotation motion-axis mode. Specifically, the rotation of the imaging element 3 relative to the two motion-axes A21, A22 can be achieved in just one rotation motion-axis mode. In addition, the rotation along the direction of the motion-axis A21 is operative by the left-direction switch 21 and the right-direction switch 22, and the rotation along the direction of the motion-axis A22 is operative by the up-direction switch 23 and the down-direction switch 24, so that the direction switch 20 can be deemed consisting of a switch pair of; the right-direction switch and left-direction switch, or the up-direction switch and down-direction switch, as the same as in the case of the straight-line motion-axis mode.

In addition, the structure according to the aspect of the Embodiment 2 is the same as the aspect of the Embodiment 1.

(Effect According to the Aspect of the Embodiment 2)

The following effect can be obtained according to the aspect of the Embodiment 2.

According to the aspect of the Embodiment 2 as set forth above, the relative location between the imaging element 3 and the table 1 is subjected to the predetermined motion-axis mode capable of shifting relative to the selected motion-axis A20 when the operation is carried out to select the predetermined motion-axis A20 from the plurality of motion-axes A20 using motion-axis selection switch 210. And when any one of a plurality of direction switches 20 is operative in the predetermined motion-axis mode, the control element 206 controls to shift the relative location between the imaging element 3 and the table 1 by the shifting mechanism 205 in the direction corresponding to the operative direction switch 20. Therefore, the motion-axis selection switch 210, which selects the motion-axis A20 among a plurality of motion-axes A20, and a plurality of direction switches 20 are combined, so that the plurality of direction switches 20 can be applied to the plurality of the motion-axes A20 at the same time.

In addition, the other effect according to the aspect of the Embodiment 2 is the same as the aspect of the Embodiment 1.

Alternative Embodiment

In addition, the aspects of the Embodiments disclosed at this time are examples and not limited thereto in any points. The scope of the present invention is specified in the claims but not in the above description of the aspect of the Embodiments and all alternative (alternative examples) are included in the scope of the claims and equivalents thereof.

According to the aspect of the Embodiments 1, 2, when subject to any motion-axis mode, the motion-axis selection switches 10, 210 and a plurality of the direction switch 20 light up, but the present invention is not limited thereto. According to the aspect of the present invention, when subject to any motion-axis mode, the motion-axis selection switches 10, 210 and a plurality of the direction switch 20 may blink or may combine lighting up and blinking.

According to the aspect of the Embodiments 1, 2, when subject to any motion-axis mode, both the motion-axis selection switches 10, 210 and a plurality of the direction switch 20 light up, but the present invention is not limited thereto. According to the aspect of the present invention, when subject to any motion-axis mode, either the motion-axis selection switches 10, 210 or a plurality of the direction switch 20 may light up.

According to the aspect of the Embodiment 1, the motion-axis selection switch 10 displays a figure capable of distinguishing a plurality of motion-axis modes each other, but the present invention is not limited thereto. According to the aspect of the present invention, the motion-axis selection switch 10, 210 may display a letter capable of distinguishing a plurality of motion-axis modes each other, or can display both a figure and a letter.

According to the aspect of the Embodiment 2, the motion-axis selection switch 210 does not display a figure capable of distinguishing a plurality of motion-axis modes each other, but the present invention is not limited thereto. According to the aspect of the Embodiment 1 of present invention, the motion-axis selection switch 10, 210 may display a letter capable of distinguishing a plurality of motion-axis modes each other, or can display both a figure and a letter as the same as the Embodiment 1.

According to the aspect of the Embodiment 1, the relative location between the imaging element 3 and the table 1 shifts by shifting the table 1 relative to the imaging element 3, and according to the aspect of the Embodiment 2, the relative location between the imaging element 3 and the table 1 shifts by shifting the imaging element 3 shifts relative to the table 1, but the present invention is not limited thereto. According to the aspect of the present invention, the relative location between the imaging element 3 and the table 1 may be shifted by shifting the imaging element 3 and the table 1 at the same time.

In addition, according to the aspect of the Embodiments 1, 2 as set forth above, the operation console 4 shifts the table 1 and the operation console 204 shifts the imaging element 3 respectively, but the present invention is not limited thereto. According to the aspect of the present invention, one operation console may shift the table 1 and the imaging element 3. In such case, as the motion-axis selection element, 4 motion-axis selection switches, i.e., the straight-line motion-axis mode switch 11 that shifts the table 1 along the straight line, the rotation motion-axis mode switch 12 that rotate-shifts the table 1, the straight-line motion-axis mode switch 211 that shifts the imaging element 3, and the rotation motion-axis mode switch 212, that rotate-shifts the imaging element 3, are installed, so that a plurality of direction switches 20 can be used at the same time in 4 motion-axis modes.

According to the aspect of the Embodiment 1 as set forth above, when the table 1 is rotate-shifted, the motion-axis A1, A2 is in-place above the examination table pedestal 2 in the z-axis direction and in addition, in-place approximately at the same height as the height of the table 1, but the present invention is not limited thereto. According to the aspect of the present invention, each location of the motion-axes A2 can be the other location in the xz-plane and yz-plane unless interfering other elements such as the examination table pedestal 2.

According to the aspect of the Embodiments 1, 2, the motion-axis selection switches 10, 210 is installed one to one of each motion-axis mode, but the present invention is not limited thereto. According to the aspect of the present invention, the different motion-axis mode may be selectable every time when the motion-axis selection switch is operative, so that only one motion-axis selection switch may be installed.

According to the aspect of the Embodiment 1 set forth above, a plurality of direction switches 20 comprises only 4 switches, i.e., the left-direction switch, the right-direction switch, the up-direction switch, and the down-direction switch, are installed, but the present invention is not limited thereto. According to the aspect of the present invention, any number of direction switches may be installed as long as at least 2. In addition, it is preferable that 2 direction switches relative to each motion-axis are installed. For example, when 2 direction switches are installed overall, either a pair of an up-direction switch and a down-direction switch, or a pair of a right-direction switch and a left-direction switch is installed, and when 8 direction switches are installed overall, a pair of the up-direction switch and the down-direction switch, a pair of the right-direction switch and the left-direction switch is installed, a pair of the up-right-direction switch and the left-down-direction switch, a pair of the right-up-direction switch and the left-down-direction switch are installed.

According to the aspect of the Embodiment 1, 2, as set forth above, the motion-axis mode is canceled when no operation takes place for 10 seconds following being subjected to the predetermined motion-axis, but the present invention is not limited thereto. According to the aspect of the present invention, the time from being subjected to the motion-axis mode to canceling the motion-axis mode can be arbitrarily set up.

According to the aspect of the Embodiments 1, 2, as set forth above, the manual-electric operation switching switch 30 switches the state, in which the operation console 4, 204 shifts the table 1 and the imaging element 3 manually and the state, in which the table 1 and the imaging element 3 are shifted by an electric operation, but the present invention is not limited thereto. According to the aspect of the present invention, the manual-electric operation switching switch 30 may be eliminated.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed, herein may be implemented as electronic hardware, computer software running on a specific purpose machine that is programmed, to carry out the operations described in this application, or combinations of both. To clearly illustrate this interchangeability of hardware and software, various illustrative components, blocks, modules, circuits, elements, features, and/or steps have been described above generally in terms of their functionality and inter-relatability. Whether such functionality is implemented as hardware or software depends upon the particular application and design constraints imposed on the overall system. Skilled computer artisans (engineers, programmers, scientists etc.) may implement the described, functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP) an Application Specific Integrated Circuit. (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as, a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and bin-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind, of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray fluoroscopic imaging apparatus, comprising:
a table on which a subject is loaded;
an imaging element that irradiates an X-ray to said subject and detects the X-ray that transmits said subject and implements at least one of an X-ray fluoroscopy and an X-ray imaging, and configuring to move a table and an imaging element in a plurality of directions of movement;
wherein the X-ray fluoroscopic imaging apparatus, further comprises:
an operation element comprising a plurality of motion-axis selection switches and a plurality of direction switches that is provided separately from said plurality of motion-axis selection switches and respectively corresponds to said plurality of directions of movement and is used in common with respect to said plurality of motion-axis selection switches, so that said same plurality of direction switches are used in common both when one of said plurality of motion-axis selection switches is used and when another of said plurality of motion-axis selection switches is used;
a memory storing at least two of the plurality of directions of movement associated with the motion axis selection switch; and
a control element;
wherein said control element includes a shifting means which shifts the table and the imaging element to a mode capable of moving the table and the imaging element in at least two directions of movement stored in association with an operated the motion-axis selection switch and moving control means which moves the table and the imaging element in the direction of movement corresponding to the operated switch among a plurality of directional switches in a mode after the transition by the shifting means.

2. The X-ray fluoroscopic imaging apparatus, according to claim 1, wherein:
said motion-axis switch provides a mode that is at least two selected from a group consisting of:

a straight-line motion-axis mode that shifts said table and said imaging element by a straight-line shifting in a direction of said motion-axis along at least one direction of a longitudinal direction of said table and a transverse direction thereof; and a rotation motion-axis mode that shifts a relative location by a rotation-shifting relative to said motion-axis selection switch along at least one direction of a longitudinal direction of said table and said transverse direction thereof; and said plurality of direction switches further comprise four switches including an up-direction switch, a down-direction switch, a right-direction switch, and a left-direction switch, wherein in the straight-line motion axis mode, when any of the four switches is continuously pressed, straight line motion is effected, and wherein in the rotation motion-axis mode, when any of the four switches is continuously pressed, a rotation motion is effected.

3. The X-ray fluoroscopic imaging apparatus, according to claim 2, wherein:

said plurality of the direction switches further comprises four switches including an up-direction switch, a down-direction switch, a right-direction switch, and a left-direction switch;

wherein at least one switch pair selected from a group consisting of: one switch pair of said up-direction switch and said down-direction switch, and one switch pair of said right-direction switch and said left-direction switch shifts said relative location by a straight-line-shifting relative to the motion-axis direction along said longitudinal direction, and the other switch pair of said direction switches said relative location by a straight-line-shifting in a motion axis direction along said transverse direction, and at least one switch pair selected from a group consisting of: said pair of said up-direction switch and said down-direction switch, and one switch pair of said right-direction switch and said left-direction switch shifts said relative location by the rotation-shifting relative to said motion-axis direction along said longitudinal direction, and the other switch pair of said direction switches shifts said relative location by a rotation-shifting relative to a motion-axis direction along said transverse direction.

4. The X-ray fluoroscopic imaging apparatus, according to claim 3, wherein:

said shifting of said relative location is carried out by shifting said table relative to said imaging element.

5. The X-ray fluoroscopic imaging apparatus, according to claim 3, wherein:

said control element cancels said motion-axis mode when no operation takes place for a time period following being subjected to said motion-axis mode.

6. The X-ray fluoroscopic imaging apparatus, according to claim 1, wherein:

said control element carries out at least one of a lighting up and a blinking of at least one of said motion-axis selection switch and said plurality of the direction switches.

7. The X-ray fluoroscopic imaging apparatus, according to claim 6, wherein:

said control element carries out said at least one of lighting one of lighting up and blinking at least one of said motion-axis selection switch and said plurality of the direction switches with a different color every motion-axis mode to one another.

8. The X-ray fluoroscopic imaging apparatus according to claim 1, wherein:

said plurality of the direction switches are installed for every motion-axis mode and indicate at least one of a figure and a letter corresponding to said motion-axis mode is displayed.

9. The X-ray fluoroscopic imaging apparatus, according to claim 2, further comprising:

a switch that switches a state, in which said relative location is manually shiftable, and a state, in which said relative location is shiftable by that said control element that controls a shifting mechanism based on an operation of said motion-axis selection switch and said plurality of direction switches.

\* \* \* \* \*